United States Patent
Reddy et al.

(10) Patent No.: US 9,024,015 B2
(45) Date of Patent: May 5, 2015

(54) PROCESS FOR PREPARING TOLVAPTAN INTERMEDIATES

(75) Inventors: Bandi Parthasaradhi Reddy, Hyderabad (IN); Kura Rathnakar Reddy, Hyderabad (IN); Dasari Muralidhara Reddy, Hyderabad (IN); Maruthi Janakiram Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 90 days.

(21) Appl. No.: 13/877,962

(22) PCT Filed: Aug. 23, 2011

(86) PCT No.: PCT/IN2011/000567
§ 371 (c)(1),
(2), (4) Date: Apr. 5, 2013

(87) PCT Pub. No.: WO2012/046244
PCT Pub. Date: Apr. 12, 2012

(65) Prior Publication Data
US 2013/0190490 A1    Jul. 25, 2013

(30) Foreign Application Priority Data

Oct. 5, 2010 (IN) .......................... 2943/CHE/2010

(51) Int. Cl.
*C07D 223/16* (2006.01)
(52) U.S. Cl.
CPC .................................. *C07D 223/16* (2013.01)

(58) Field of Classification Search
CPC ....................................................... C07D 223/16
USPC ............................................................ 540/593
See application file for complete search history.

(56) References Cited

U.S. PATENT DOCUMENTS 4,009,208 A    2/1977    Lesher

FOREIGN PATENT DOCUMENTS

WO    2007026971 A1    3/2007

OTHER PUBLICATIONS

International Search Report and Written Opinion; International Application No. PCT/IN 11/00567; International Filing Date Aug. 23, 2011; Earliest Priority Date Oct. 5, 2010; Date of Mailing Mar. 20, 2012; Agent Reference No. HET0101US; 6 pages.
Kondo et al.; "7-Chloro-5-hydroxy-1[2-methyl-4-(2-methylbenzoyl-amino)benzoyl]-2,3,4,5-tetrahydro-1H-1-benzazepine (OPC-41061): a Potent, Orally Active Nonpeptide Arginine Vasopressin V2 Receptor Antagonist"; Bioorganic & Medicinal Chemistry; 7; pp. 1743-1754; (1999).

*Primary Examiner* — Brenda Coleman
(74) *Attorney, Agent, or Firm* — Cantor Colburn LLP

(57) ABSTRACT

The present invention provides a novel process for the preparation of 7-chloro-2,3,4,5-tetrahydro-1H-1-benzazepin-5-one. The present invention also provides an improved process for the preparation of 7-chloro-1-(2-methyl-4-nitrobenzoyl)-5-oxo-2,3,4,5-tetrahydro-1H-1-benzazepine. The present invention further provides an improved process for the preparation of 7-chloro-1-[2-methyl-4-[(2-methylbenzoyl)amino]benzoyl]-5-oxo-2,3,4,5-tetrahydro-1H-1-benzazepine.

15 Claims, No Drawings

PROCESS FOR PREPARING TOLVAPTAN INTERMEDIATES

CROSS-REFERENCE TO RELATED APPLICATIONS

This application is a 371 Application of PCT/IN2011/000567, filed Aug. 23, 2011 which claims the benefit of priority to Indian Patent Application No. 2943/CHE/2010, filed on Oct. 05, 2010 under the provisions of 35 U.S.C. §119 and the International Convention for the protection of Industrial Property, which are incorporated herein by reference in their entirety.

FILED OF THE INVENTION

The present invention provides a novel process for the preparation of 7-chloro-2,3,4,5-tetrahydro-1H-1-benzazepin-5-one. The present invention also provides an improved process for the preparation of 7-chloro-1-(2-methyl-4-nitrobenzoyl)-5-oxo-2,3,4,5-tetrahydro-1H-1-benzazepine. The present invention further provides an improved process for the preparation of 7-chloro-1-[2-methyl-4-[(2-methylbenzoyl)amino]benzoyl]-5-oxo-2,3,4,5-tetrahydro-1H-1-benzazepine.

BACKGROUND OF THE INVENTION

Tolvaptan is chemically, N-[4-[(7-chloro-2,3,4,5-tetrahydro-5-hydroxy1H-1-benzazepin-1-yl)carbonyl]-3-methylphenyl]-2-methylbenzamide. Tolvaptan is represented by the following structure:

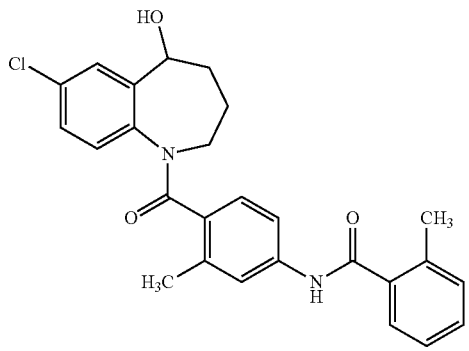 [SMILES: Cc1ccccc1C(=O)Nc1ccc(C(=O)N2CCCC(O)c3cc(Cl)ccc32)c(C)c1]

Tolvaptan, also known as OPC-41061, is a selective, competitive arginine vasopressin receptor 2 antagonist used to treat hyponatremia (low blood sodium levels) associated with congestive heart failure, cirrhosis, and the syndrome of inappropriate antidiuretic hormone (SIADH). Tolvaptan is sold by Otsuka Pharmaceutical Co. under the trade name Samsca.

Tolvaptan and its process for preparation were disclosed in U.S. Pat. No. 5,258,510.

Processes for the preparation of 7-chloro-2,3,4,5-tetrahydro-1H-1-benzazepin-5-one, 7-chloro-1-(2-methyl-4-nitrobenzoyl)-5-oxo-2,3,4,5-tetrahydro-1H-1-benzazepine and 7-chloro-1-[2-methyl-4-[(2-methylbenzoyl)amino]benzoyl]-5-oxo-2,3,4,5-tetrahydro-1H-1-benzazepine were reported in *Bioorganic & medicinal chemistry* 7 (1999), 1743-1754. According to the journal, 7-chloro-2,3,4,5-tetrahydro-1H-1-benzazepin-5-one can be prepared by reacting 7-chloro-4-ethoxycarbonyl-5-oxo-N-p-toluenesufonyl-2,3,4,5-tetrahydro-1H-1-benzazepine with acetic acid in the presence of hydrochloric acid and water to obtain 7-chloro-5-oxo-2,3,4,5-tetrahydro-1-p-toluenesulfonyl-1H-1-benzazepine, and then reacted with polyphospholic acid.

According to the journal, 7-chloro-1-(2-methyl-4-nitrobenzoyl)-5-oxo-2,3,4,5-tetrahydro-1H-1-benzazepine can be prepared by reacting 7-chloro-5-oxo-2,3,4,5-tetrahydro-1H-1-benzazepine with 2-methyl-4-nitobenzoyl chloride in the presence of triethylamine.

According to the journal, 7-chloro-1-[2-methyl-4-[(2-methylbenzoyl)amino]benzoyl]-5-oxo-2,3,4,5-tetrahydro-1H-1-benzazepine can be prepared by reacting 1-(4-amino-2-methylbenzoyl)-7-chloro-5-oxo-2,3,4,5-tetrahydro-1H-1-benzazepine with 2-methylbenzoylchloride in the presence of triethylamine.

PCT publication no. WO 2007/026971 disclosed a process for the preparation of tolvaptan can be prepared by the reduction of 7-chloro-1-[2-methyl-4-(2-methylbenzoylamino)benzoyl]-2,3,4,5-tetrahydro-1H-1-benzazepin-5-one with sodium borohydride.

7-Chloro-2,3,4,5-tetrahydro-1H-1-benzazepin-5-one is a key intermediate for the preparation of tolvaptan.

We have discovered a novel process for the preparation of 7-chloro-2,3,4,5-tetrahydro-1H-1-benzazepin-5-one.

7-Chloro-1-(2-methyl-4-nitrobenzoyl)-5-oxo-2,3,4,5-tetrahydro-1H-1-benzazepine is a key intermediate for the preparation of tolvaptan.

We have also discovered an improved process for the preparation of 7-chloro-1-(2-methyl-4-nitrobenzoyl)-5-oxo-2,3,4,5-tetrahydro-1H-1-benzazepine. The process of the invention results in higher yields compared with the known process of using organic base in the reaction.

7-Chloro-1-[2-methyl-4-[(2-methylbenzoyl)amino]benzoyl]-5-oxo-2,3,4,5-tetrahydro-1H-1-benzazepine is a key intermediate for the preparation of tolvaptan.

We have also discovered an improved process for the preparation of 7-chloro-1-[2-methyl-4-[(2-methylbenzoyl)amino]benzoyl]-5-oxo-2,3,4,5-tetrahydro-1H-1-benzazepine. The process of the invention results in higher yields compared with the known process of using organic base in the reaction.

Thus, an object of the present invention is to provide a novel process for the preparation of 7-chloro-5-oxo-2,3,4,5-tetrahydro-1H-1-benzazepine.

Another object of the present invention is to provide an improved process for the preparation of 7-chloro-1-(2-methyl-4-nitrobenzoyl)-5-oxo-2,3,4,5-tetrahydro-1H-1-benzazepine.

Yet another object of the present invention is to provide an improved process for the preparation of 7-chloro-1-[2-methyl-4-[(2-methylbenzoyl)amino]benzoyl]-5-oxo-2,3,4,5-tetrahydro-1H-1-benzazepine.

SUMMARY OF THE INVENTION

In one aspect, the present invention provided a novel process for the preparation of 7-chloro-5-oxo-2,3,4,5-tetrahydro-1H-1-benzazepine, which comprises:
a) reacting the 7-chloro-4-ethoxycarbonyl-5-oxo-N-p-toluenesufonyl-2,3,4,5-tetrahydro-1H-benzazepine with sulfuric acid;
b) maintaining the contents obtained in step (a) at above 50° C.;
c) cooling the reaction mass obtained in step (b) at room temperature;
d) pouring the reaction mass to the water;
e) adjusting the pH of the reaction mass to about 7.0 to 8.5 with a base; and f) isolating 7-chloro-5-oxo-2,3,4,5-tetrahydro-1H-1-benzazepine.

In another aspect, the present invention provided an improved process for the preparation of 7-chloro-1-(2-methyl-4-nitrobenzoyl)-5-oxo-2,3,4,5-tetrahydro-1H-1-benzazepine, which comprises reacting 7-chloro-5-oxo-2,3,4,5-tetrahydro-1H-1-benzazepine with 2-methyl-4-nitobenzoylchloride in the presence of an inorganic base.

In yet another aspect, the present invention provided an improved process for the preparation of 7-chloro-1-[2-methyl-4-[(2-methylbenzoyl)amino]benzoyl]-5-oxo-2,3,4,5-tetrahydro-1H-1-benzazepine, which comprises reacting 1-(4-amino-2-methylbenzoyl)-7-chloro-5-oxo-2,3,4,5-tetrahydro-1H-1-benzazepine with 2-methylbenzoylchloride in the presence of an inorganic base.

DETAILED DESCRIPTION OF THE INVENTION

The term "room temperature" refers to temperature at about 25 to 35° C.

According to one aspect of the present invention, there is provided a novel process for the preparation of 7-chloro-5-oxo-2,3,4,5-tetrahydro-1H-1-benzazepine, which comprises:

a) reacting the 7-chloro-4-ethoxycarbonyl-5-oxo-N-p-toluenesufonyl-2,3,4,5-tetrahydro-1H-benzazepine with sulfuric acid;
b) maintaining the contents obtained in step (a) at above 50° C.;
c) cooling the reaction mass obtained in step (b) at room temperature;
d) pouring the reaction mass to the water;
e) adjusting the pH of the reaction mass to about 7.0 to 8.5 with a base; and
f) isolating 7-chloro-5-oxo-2,3,4,5-tetrahydro-1H-1-benzazepine.

Sulfuric acid used in step (a) may be in the form of aqueous sulfuric acid.

Step (b) may preferably be carried out at about 60 to 100° C. and more preferable at about 65 to 85° C.

Preferably the water used in step (d) may be ice water.

The base used in step (e) may preferably be an organic base or inorganic base and more preferably the base is inorganic base selected from alkali metal hydroxides, alkali metal carbonates or alkali metal bicarbonates. Still more preferably the inorganic base is sodium hydroxide or potassium hydroxide.

Preferably the pH in step (e) may be adjusted to 7.2 to 8.2 and more preferably the pH is adjusted to 7.5 to 8.0.

The isolation of 7-chloro-5-oxo-2,3,4,5-tetrahydro-1H-1-benzazepine in step (f) may preferably be performed by conventional techniques such as centrifugation and filtration.

According to another aspect of the present invention, there is provided an improved process for the preparation of 7-chloro-1-(2-methyl-4-nitrobenzoyl)-5-oxo-2,3,4,5-tetrahydro-1H-1-benzazepine, which comprises reacting 7-chloro-5-oxo-2,3,4,5-tetrahydro-1H-1-benzazepine with 2-methyl-4-nitrobenzoylchloride in the presence of an inorganic base.

Preferably the inorganic base may be used in the form of aqueous inorganic base. More preferably the aqueous inorganic base is selected from alkali metal hydroxides, alkali metal carbonates or alkali metal bicarbonates. Still more preferably the aqueous inorganic base is aqueous sodium bicarbonate, aqueous sodium carbonate or aqueous potassium carbonate.

Typically, 7-chloro-5-oxo-2,3,4,5-tetrahydro-1H-1-benzazepine is reacted with 2-methyl-4-nitrobenzoylchloride in water immiscible solvent selected from methylene chloride, toluene or cyclohexane in the presence of aqueous inorganic base such as aqueous sodium bicarbonate or aqueous sodium carbonate to form a biphasic system to obtain 7-chloro-1-(2-methyl-4-nitrobenzoyl)-5-oxo-2,3,4,5-tetrahydro-1H-1-benzazepine.

According to another aspect of the present invention, there is provided an improved process for the preparation of 7-chloro-1-[2-methyl-4-[(2-methylbenzoyl)amino]benzoyl]-5-oxo-2,3,4,5-tetrahydro-1H-1-benzazepine, which comprises reacting 1-(4-amino-2-methylbenzoyl)-7-chloro-5-oxo-2,3,4,5-tetrahydro-1H-1-benzazepine with 2-methylbenzoylchloride in the presence of an inorganic base.

Preferably the inorganic base may be used in the form of aqueous inorganic base. More preferably the aqueous inorganic base is selected from alkali metal hydroxides, alkali metal carbonates or alkali metal bicarbonates. Still more preferably the aqueous inorganic base is aqueous sodium bicarbonate, aqueous sodium carbonate or aqueous potassium carbonate.

Typically, 1-(4-amino-2-methylbenzoyl)-7-chloro-5-oxo-2,3,4,5-tetrahydro-1H-1-benzazepine is reacted with 2-methylbenzoylchloride in water immiscible solvent selected from methylene chloride, toluene or cyclohexane in the presence of aqueous inorganic base such as aqueous sodium bicarbonate or aqueous sodium carbonate to form a biphasic system to obtain 7-chloro-1-[2-methyl-4-[(2-methylbenzoyl)amino]benzoyl]-5-oxo-2,3,4,5-tetrahydro-1H-1-benzazepine.

Tolvaptan can be prepared by the known process, for example, by reducing the 7-chloro-1-[2-methyl-4-[(2-methylbenzoyl)amino]benzoyl]-5-oxo-2,3,4,5-tetrahydro-1H-1-benzazepine with sodium borohydride in an alcoholic solvent to obtain tolvaptan.

The alcoholic solvent used in the process may preferably be a solvent or mixture of solvents selected from methanol, ethanol, isopropyl alcohol, tert-butyl alcohol, n-butanol and isobutyl alcohol. More preferably the alcoholic solvent is methanol.

The invention will now be further described by the following examples, which are illustrative rather than limiting.

REFERENCE EXAMPLES

Reference Example 1

Preparation of Methyl 5-chloro-2-nitrobenzoate

Potassium carbonate (515 gm) was added to a solution of 5-chloro-2-nitro benzoic acid (500 gm) in acetone (2750 ml) at room temperature. Dimethyl sulphate (306.5 gm) was added to the reaction mixture slowly and heated to reflux for 30 minutes. The reaction mass was filtered and then concentrated to obtain a residual mass. The residual mass was poured to the ice water and extracted with methylene chloride. The solvent was distilled off under reduced pressure to obtain a residual solid of methyl 5-chloro-2-nitrobenzoate (534 gm).

Reference Example 2

Preparation of Methyl 2-amino-5-chlorobenzoate

A mixture of methyl 5-chloro-2-nitrobenzoate (534 gm) as obtained in reference example 1 and concentrated hydrochloric acid (2250 ml) was added to ethyl acetate (1120 ml). To the reaction mixture was added a solution of tin chloride (1680 gm) in ethyl acetate (2250 ml). The reaction mass was stirred for 16 hours at room temperature and then poured to the ice water. The pH of the reaction mass was adjusted to 8.0 to 9.0 with aqueous sodium hydroxide solution (2650 ml). The separated aqueous layer was extracted with ethyl acetate and then concentrated to obtain a residual solid of methyl 2-amino-5-chlorobenzoate (345 gm).

Reference Example 3

Preparation of Methyl 5-chloro-2-(N-p-toluenesulfonyl)aminobenzoate

To a solution of methyl-2-amino-5-chloro benzoate (345 gm) as obtained in reference example 2 in pyridine (1725 ml) was added p-toluenesulfonyl chloride (425 gm). The reaction mixture was stirred for 2 hours at room temperature and poured to the ice water. The separated solid was filtered and dried to obtain 585 gm of methyl 5-chloro -2-(N-p-toluenesulfonyl)aminobenzoate.

Reference Example 4

Preparation of methyl 5-chloro-2-[N-(3-ethoxycarbonyl)propyl-N-p-toluenesulfonyl]aminobenzoate Methyl 5-chloro-2-(N-p-taluenesulfonyl)aminobenzoate (585 gm) as obtained in reference example 3, ethyl-4-bromo butyrate (369.6 gm) and potassium carbonate (664 gm) in dimethylformamide (4400 ml) were added at room temperature. The contents were heated to 120° C. and maintained for 2 hours. The reaction mass was poured into water and filtered. The solid obtained was dried to give 726 gm of methyl 5-chloro-2-[N-(3-ethoxycarbonyl)propyl-N-p-toluenesulfonyl]aminobenzoate.

Reference Example 5

Preparation of 7-chloro-4-ethoxycarbonyl-5-oxo-N-p-toluenesufonyl-2,3,4,5-tetrahydro-1H-1-benzazepine To a heated mixture of potassium tetrabutoxide (363 gm) in toluene (1000 ml) at 70° C. was added portion wise methyl 5-chloro-2-[N-(3-ethoxycarbonyl)propyl-N-p-toluenesulfonyl]aminobenzoate (726 gm) as obtained in reference example 4. The contents were heated to reflux and maintained for 30 minutes. The reaction mass was then cooled to room temperature and then poured to the ice water. The layers were separated and the aqueous layer was extracted with toluene. The solvent was distilled off under reduced pressure to obtain a residual solid of 7-chloro-4-ethoxycarbonyl-5-oxo-N-p-toluenesufonyl-2,3,4,5-tetrahydro-1H-1-benzazepine (455 gm).

EXAMPLES

Example 1

Preparation of 7-chloro-5-oxo-2,3,4,5-tetrahydro-1H-1-benzazepine

7-Chloro-4-ethoxycarbonyl-5-oxo-N-p-toluenesufonyl-2,3,4,5-tetrahydro-1H-1-benzazepine (455 gm) as obtained in reference example 5 was added to aqueous sulfuric acid (80%, 2275 ml). The contents heated to 75° C. and maintained for 2 hours. The reaction mass was then cooled to room temperature and then poured to the ice water. The pH of the reaction mass was adjusted to 7.5 to 8.0 with sodium hydroxide solution (2575 ml). The solid obtained was collected by filtration and dried to give 160 gm of 7-chloro-5-oxo-2,3,4,5-tetrahydro-1H-1-benzazepine.

Example 2

Preparation of 7-chloro-1-(2-methyl-4-nitrobenzoyl)-5-oxo-2,3,4,5-tetrahydro-1H-1-benzazepine 7-Chloro-5-oxo-2,3,4,5-tetrahydro-1H-1-benzazepine (160 gm) as obtained in example 1 was dissolved in methylene dichloride (480 ml) and then added aqueous sodium bicarbonate solution (20%, 68.75 gm). The reaction mixture was then cooled to 0 to 5° C. and then added 2-methyl-4-nitrobenzoylchloride (180 gm) slowly. The pH of the reaction mass was adjusted to 7.0 to 8.0 with aqueous sodium bicarbonate solution (170 ml). The layers were separated and the aqueous layer was extracted with methylene chloride. The solvent was distilled off under reduced pressure to obtain a residual mass.

To the residual mass was dissolved in isopropyl alcohol (7300 ml) and maintained for 2 hours at reflux temperature. The separated solid was filtered and dried to obtain 250 gm of 7-chloro-1-(2-methyl-4-nitrobenzoyl)-5-oxo-2,3,4,5-tetrahydro-1H-1-benzazepine.

Example 3

Preparation of 1-(4-amino-2-methylbenzoyl)-7-chloro-5-oxo-2,3,4,5-tetrahydro-1H-1-benzazepine 7-Chloro-1-(2-methyl-4-nitrobenzoyl)-5-oxo-2,3,4,5-tetrahydro-1H-1-benzazepine (250 gm) as obtained in example 2 was dissolved in methanol (575 ml) and then added a solution of tin chloride (630 gm) in methanol (1130 ml). The reaction mixture was stirred for 16 hours at room temperature and then poured to the ice water. The pH of the reaction mass was adjusted to 8.0 to 9.0 with sodium hydroxide solution (1250 ml). The layers were separated and the aqueous layer was extracted with ethyl acetate. The solvent was distilled off under vacuum to obtain a residual solid of 1-(4-amino-2-methylbenzoyl)-7-chloro-5-oxo-2,3,4,5-tetrahydro-1H-1-benzazepine (185 gm).

Example 4

Preparation of 7-chloro-1-[2-methyl-4-[(2-methylbenzoyl)amino]benzoyl]-5-oxo-2,3,4,5-tetrahydro-1H-1-benzazepine 1-(4-Amino-2-methylbenzoyl)-7-chloro-5-oxo-2,3,4,5-tetrahydro-1H-1-benzazepine (185 gm) as obtained in example 3 was dissolved in methylene chloride (4000 ml) and then added sodium bicarbonate solution (10%, 47.3 gm). The reaction mass was cooled to 0 to 5° C. and then added 2-methyl benzoyl chloride (95.7 gm) slowly. The pH of the reaction mass was adjusted to 7.0 to 8.0 with aqueous sodium bicarbonate solution (120 ml). The separated aqueous layer was extracted with methylene chloride and then concentrated to obtain a residual solid of 7-chloro-1-[2-methyl-4-[(2-methylbenzoyl)amino]benzoyl]-5-oxo-2,3,4,5-tetrahydro-1H-1-benzazepine (185 gm).

Example 5

Preparation of Tolvaptan

7-Chloro-1-[2-methyl-4-[(2-methylbenzoyl)amino]benzoyl]-5-oxo-2,3,4,5-tetrahydro-1H-1-benzazepine (63 gm)

as obtained in example 4 was dissolved in methanol (570 ml) and then added sodium borohydride (2.07 gm) at room temperature. The reaction mass was stirred for 1 hour and pH of the reaction mass was adjusted to 6.0 to 7.0 with hydrochloric acid solution (1%, 630 ml). The separated solid was filtered and dried to obtain 57 gm of tolvaptan.

We claim:

1. A process for the preparation of 7-chloro-5-oxo-2,3,4,5-tetrahydro-1H-1-benzazepine, comprising:
    a) reacting 7-chloro-4-ethoxycarbonyl-5-oxo-N-p-toluenesufonyl-2,3,4,5-tetrahydro-1H-benzazepine with sulfuric acid;
    b) maintaining the contents obtained in step (a) at above 50° C. to form reaction mass;
    c) cooling the first reaction mass obtained in step (b) at room temperature;
    d) pouring the reaction mass into water;
    e) adjusting the pH of the reaction mass to about 7.0 to 8.5 with a base; and
    f) isolating 7-chloro-5-oxo-2,3,4,5-tetrahydro-1H-1-benzazepine from the reaction mass.

2. The process of claim 1, wherein the sulfuric acid is used in step (a) in the form of aqueous sulfuric acid.

3. The process of claim 1, wherein step (b) is carried out at a temperature of about 60 to 100° C.

4. The process of claim 1, wherein the base used in step (e) is an organic base or inorganic base.

5. The process of claim 4, wherein the base is an inorganic base selected from alkali metal hydroxides, alkali metal carbonates and alkali metal bicarbonates.

6. The process of claim 5, wherein the inorganic base is selected from sodium hydroxide and potassium hydroxide.

7. The process of claim 1, wherein the pH in step (e) is adjusted to 7.2 to 8.2.

8. A process for the preparation of 7-chloro-1-(2-methyl-4-nitrobenzoyl)-5-oxo-2,3,4,5-tetrahydro-1H-1-benzazepine, comprising reacting 7-chloro-5-oxo-2,3,4,5-tetrahydro-1H-1-benzazepine with 2-methyl-4-nitrobenzoyl chloride in the presence of an inorganic base.

9. The process of claim 8, wherein the inorganic base is used in the form of aqueous inorganic base.

10. The process of claim 9, wherein the aqueous inorganic base is selected from alkali metal hydroxides, alkali metal carbonates and alkali metal bicarbonates.

11. The process of claim 10, wherein the aqueous inorganic base is selected from aqueous sodium bicarbonate, aqueous sodium carbonate and aqueous potassium carbonate.

12. A process for the preparation of 7-chloro-1-[2-methyl-4-[(2-methylbenzoyl)amino]benzoyl]-5-oxo-2,3,4,5-tetrahydro-1H-1-benzazepine, comprising reacting 1-(4-amino-2-methylbenzoyl)-7-chloro-5-oxo-2,3,4,5-tetrahydro-1H-1-benzazepine with 2-methylbenzoylchloride in the presence of an inorganic base.

13. The process of claim 12, wherein the inorganic base is used in the form of aqueous inorganic base.

14. The process of claim 13, wherein the aqueous inorganic base is selected from alkali metal hydroxides, alkali metal carbonates and alkali metal bicarbonates.

15. The process of claim 14, wherein the aqueous inorganic base is aqueous sodium bicarbonate, aqueous sodium carbonate or aqueous potassium carbonate.

* * * * *